United States Patent
Fujita et al.

[11] Patent Number: 6,143,911
[45] Date of Patent: *Nov. 7, 2000

[54] CATALYST USEFUL FOR THE POLYMERIZATION OF OLEFINS

[75] Inventors: Takashi Fujita; Toshihiko Sugano; Hideshi Uchino, all of Yokkaichi, Japan

[73] Assignee: Mitsubishi Petrochemical Company Limited, Tokyo-To, Japan

[*] Notice: Under 35 U.S.C. 154(b), the term of this patent shall be extended for 378 days. This patent is subject to a terminal disclaimer.

[21] Appl. No.: 08/678,686

[22] Filed: Jul. 11, 1996

Related U.S. Application Data

[62] Division of application No. 08/445,556, May 22, 1995, Pat. No. 5,561,093, which is a continuation of application No. 07/933,215, Aug. 20, 1992, abandoned.

Foreign Application Priority Data

Aug. 20, 1991 [JP] Japan ................. 3-208213

[51] Int. Cl.$^7$ ................. C07F 17/00; C07F 7/00
[52] U.S. Cl. ................. 556/11; 556/53; 502/103; 502/117; 526/160; 526/943
[58] Field of Search ................. 556/11, 53, 56; 526/160, 943; 502/103, 117

[56] References Cited

U.S. PATENT DOCUMENTS

| | | | |
|---|---|---|---|
| 4,871,705 | 10/1989 | Hoel ................. | 502/117 |
| 5,120,867 | 6/1992 | Welborn, Jr. ................. | 556/12 |
| 5,145,819 | 9/1992 | Winter et al. ................. | 502/117 |
| 5,329,033 | 7/1994 | Spaleck et al. ................. | 556/53 |
| 5,374,752 | 12/1994 | Winter et al. ................. | 556/11 |

FOREIGN PATENT DOCUMENTS

| | | |
|---|---|---|
| 0 344 887 | 12/1989 | European Pat. Off. . |
| 0 366 290 | 5/1990 | European Pat. Off. . |
| 0 485 822 | 5/1992 | European Pat. Off. . |
| WO 90/07526 | 7/1990 | WIPO . |

*Primary Examiner*—Porfirio Nazario-Gonzalez
*Attorney, Agent, or Firm*—Oblon, Spivak, McClelland, Maier & Neustadt, P.C.

[57] ABSTRACT

A catalyst useful for the polymerization of olefins, comprising the following components (A) and (B):

Component (A): A transition metallic compound having the following formula [I]:

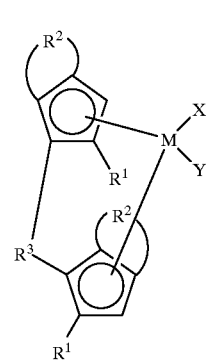

[I]

wherein M: a transition metal selected from Ti, Zr and Hf;

$R^1$: a monovalent $C_{1-6}$ hydrocarbyl group, or a monovalent $C_{1-6}$ hydrocarbyl group containing Si;

$R^2$: a divalent $C_{4-20}$ hydrocarbyl group, or a divalent $C_{4-20}$ hydrocarbyl group containing Si;

$R^3$: a divalent $C_{1-30}$ hydrocarbyl group, or a divalent $C_{1-30}$ hydrocarbyl group containing Si or Ge; and X and Y: H, halogen, a monovalent $C_{1-20}$ hydrocarbyl group, or a monovalent $C_{1-20}$ hydrocarbyl group containing N, O or Si.

Component (B): Alumoxane having the following formula [II] or [III]:

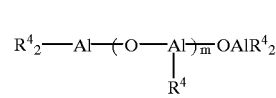

[II]

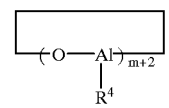

[III]

wherein m: 4 to 30; and $R^4$: a monovalent hydrocarbyl group.

A highly stereoregular polyolefin having a high molecular weight can be obtained by the above catalyst.

12 Claims, No Drawings

CATALYST USEFUL FOR THE POLYMERIZATION OF OLEFINS

This is a Division of application Ser. No. 08/445,556 filed on May 22, 1995, now U.S. Pat. No. 5,561,093, which is a Continuation of application Ser. No. 07/933,215 filed Aug. 20, 1992, abandoned.

BACKGROUND OF THE INVENTION

1. Field of the Invention

The present invention relates to a catalyst for use in the production of stereoregular polyolefins. More specifically, the present invention relates to a catalyst which is useful for the polymerization of olefins and comprises a specific metallocene compound which is a novel asymmetric transition metallic compound having bis-substituted-cyclopentadienyl-bridge-type bidentate ligands of bridge structure, and alumoxane.

2. Related Art

A so-called Kaminsky catalyst comprising a metallocene compound and alumoxane has been well known as a homogeneous catalyst useful for the polymerization of olefins. This catalyst is characterized in that it brings about extremely high polymerization activity, and that it can produce a polymer with a narrow molecular weight distribution.

Ethylenebis(indenyl)zirconium dichloride and ethylenebis(4,5,6,7-tetrahydroindenyl)zirconium dichloride (Japanese Patent Application Laid-Open Publication No. 130314/1986) have been known as transition metallic compounds useful for the production of isotactic polyolefins. They are, however, disadvantageous in that they produce polyolefins having low molecular weights, and that they can produce polyolefins having high molecular weights if the production is conducted at a low temperature, but, in this case, the polymerization activity is low.

Further, it has been known that a polymer having a high molecular weight can be produced when a hafnium compound is used instead of zirconium (Journal of Molecular Catalysis, 56 (1989) p. 237–247). However, this method has a shortcoming in that the polymerization activity is low.

Furthermore, dimethylsilylbis-substituted cyclopentadienylzirconium dichloride and the like are described in Japanese Patent Application Laid-Open Publication No. 301704/1989, Polymer Preprints, Japan Vol. 39, No. 6, p. 1614–1616 (1990), Japanese Patent Application Laid-Open Publication No. 12406/1991 and the like. However, there is no report concerning a catalyst which can bring about high polymerization activity and, at the same time, can give a polymer having a high molecular weight.

An object of the present invention is to provide a polymerization method by which a propylene polymer having a high molecular weight (number-average molecular weight: 70,000 or more), capable of being subjected to both extrusion molding and injection molding, can be obtained in high yield.

SUMMARY OF THE INVENTION

The present invention has been accomplished as a result of the studies which were made to solve the above-described problems. More specifically, the catalyst useful for the polymerization of olefins according to the present invention comprises the following component (A) and component (B):

Component (A): A transition metallic compound having the following formula [I]:

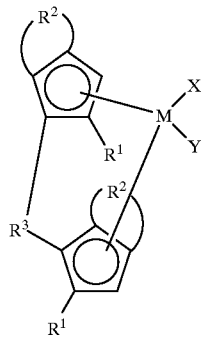

wherein: M represents a transition metal selected from the group consisting of titanium, zirconium and hafnium;

two $R^1$s may be the same or different, and represent a monovalent hydrocarbyl group having 1 to 6 carbon atoms, or a monovalent hydrocarbyl group having 1 to 6 carbon atoms and containing silicon;

two $R^2$s may be the same or different, and represent a divalent hydrocarbyl group having 4 to 20 carbon atoms, or a divalent hydrocarbyl group having 4 to 20 carbon atoms and containing silicon, which residue is bonded to two adjacent carbon atoms of the five-membered cyclic ligand;

$R^3$ represents a divalent hydrocarbyl group having 1 to 30 carbon atoms in total, or a divalent hydrocarbyl group having 1 to 30 carbon atoms in total and containing silicon or germanium; and X and Y independently represent hydrogen, halogen, a monovalent hydrocarbyl group having 1 to 20 carbon atoms, or a monovalent hydrocarbyl group having 1 to 20 carbon atoms and containing nitrogen, oxygen or silicon, provided that the two five-membered cyclic ligands each having the substituents $R^1$ and $R^2$ are asymmetric about a plane containing M when viewed from their relative position in terms of the group $R^3$.

Component (B): Alumoxane having the following formula [II] or [III]:

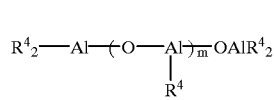

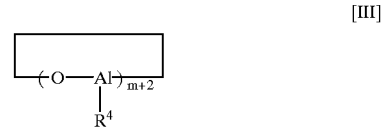

wherein m is a number of 4 to 30, and $R^4$ is a monovalent hydrocarbyl group.

By using the catalyst according to the present invention, a stereoregular polyolefin having a high molecular weight can be produced in high yield.

It is due to the characteristic features of the present invention such as the use of the asymmetric metallocene compound that the objects sought, that is, to make the polymerization activity high and to produce high-molecular-weight polymers, which are fundamentally incompatible with each other, can be successfully attained at the same time. This is considered to be an unexpected finding.

DESCRIPTION OF THE PREFERRED EMBODIMENTS

Catalyst

The present invention relates to a catalyst useful for the polymerization of olefins, comprising component (A) and component (B) as shown below. The expression "comprising component (A) and component (B)" herein means that it is possible to use a third component other than components (A) and (B) as long as it does not impair the effects of the present invention.

<Component (A)>

Component (A) which is used as one component of the catalyst of the present invention is a transition metallic compound represented by the following formula [I]:

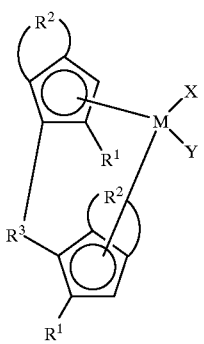

[I]

wherein M represents a transition metal selected from the group consisting of titanium, zirconium and hafnium;

two $R^1$s may be the same or different, and represent a monovalent hydrocarbyl group having 1 to 6, preferably 1 to 4 carbon atoms, or a monovalent hydrocarbyl group having 1 to 6, preferably 1 to 4 carbon atoms, and containing silicon;

two $R^2$s may be the same or different, and represent a divalent hydrocarbyl group having 4 to 20, preferably 4 to 8 carbon atoms, or a divalent hydrocarbyl group having 4 to 20, preferably 4 to 8 carbon atoms, and containing silicon, which residue is bonded to two adjacent carbon atoms of the five-membered cyclic ligand;

$R^3$ represents a divalent hydrocarbyl group having 1 to 30, preferably 2 to 20 carbon atoms in total, or a divalent hydrocarbyl group having 1 to 30, preferably 2 to 20 carbon atoms in total, containing silicon or germanium; and X and Y independently represent hydrogen, halogen, a monovalent hydrocarbyl group having 1 to 20, preferably 1 to 7 carbon atoms, or a monovalent hydrocarbyl group having 1 to 20, preferably 1 to 7 carbon atoms, containing nitrogen, oxygen or silicon.

The distinctive feature of the metallocene compound having the formula [I] for use in the present invention is that the two five-membered cyclic ligands contained in the compound, each having the substituents $R^1$ and $R^2$ are asymmetric about a plane containing M when viewed from their relative position in terms of the group $R^3$.

The expression "asymmetric about a plane containing M when viewed from their relative position in terms of the group $R^3$" means that the relationship between the two substituted five-membered rings which are facing each other with M (more precisely, X—M—Y) therebetween is not equivalent to the relationship between an object and its mirror image.

In the above case, the state of asymmetry can be roughly divided into two types. One of them is such that the relationship between the two substituted five-membered cyclic ligands with respect to a plane containing M, X and Y is not equivalent to that between an object and its mirror image in terms of the positions of $R^1$ and $R^2$. In this case, even if $R^1$s and $R^2$s contained in the two substituted five-membered cyclic ligands are respectively the same, the relationship between the two substituted ligands is not equivalent to that between an object and its mirror image.

Another type of asymmetry is such that although the relationship between the two substituted ligands is equivalent to that between an object and its mirror image in terms of the respective positions of the substituents $R^1$ and $R^2$, at least either $R^1$s or $R^2$s are not the same between the two five-membered cyclic ligands. For instance, even when the positional relationship between the two $R^1$s is equivalent to the relationship between an object and its mirror image, the relationship between the two five-membered cyclic ligands is not equivalent to the relationship between an object and its mirror image because the types of $R^1$s are different from each other. In the present invention, only the former type of state is referred to as the state of asymmetry.

As described above, $R^1$ is a monovalent hydrocarbyl group having 1 to 6 carbon atoms, or a monovalent hydrocarbyl group having 1 to 6 carbon atoms, containing silicon. More specifically, $R^1$ is a saturated hydrocarbon group such as alkyl or cycloalkyl, an unsaturated hydrocarbon group such as alkenyl, or a hydrocarbon group containing silicon such as alkylsilyl. Specific examples of $R^1$ include methyl, ethyl, n-propyl, i-propyl, n-butyl, i-butyl, t-butyl, n-amyl, i-amyl, n-hexyl, cyclopropyl, allyl, trimethylsilyl and dimethylethylsilyl groups. Of these groups, lower alkyl groups such as methyl, ethyl, n-propyl, i-propyl, n-butyl, i-butyl and t-butyl are preferred.

$R^2$ is, more specifically, a saturated hydrocarbon group such as alkylene or cycloalkylene, an unsaturated hydrocarbon group such as alkadienylene or arylene, or a hydrocarbon group containing silicon such as alkylsilylalkylene or alkylsilylalkenylene, which forms a 4- to 8-membered ring, preferably a 6-membered ring together with the cyclopentadienyl group to which $R^2$ is bonded. Specific examples of $R^2$ include butylene, methylbutylene, 2-methylbutylene, 1,2-dimethylbutylene, cyclopropylbutylene, 1,3-butadienylene, methyl-1,3-butadienylene, phenylbutylene, phenyl-1,3-butadienylene, trimethylsilylbutylene, trimethylsilyl-1,3-butadienylene, dimethylethylsilylbutylene, dimethylethylsilyl-1,3-butadienylene groups. Of these groups, alkylene groups such as butylene and methylbutylene, in particular, n-butylene group, and alkadienylene groups such as 1,3-butadienylene and methyl-1,3-butadienylene, in particular, 1,3-butadienylene group are preferred.

$R^3$ is, more specifically, a saturated hydrocarbyl group such as lower alkylene or cycloalkylene, which can be substituted by a hydrocarbyl group, provided that the total number of carbon atom is 1 to 30; an unsaturated hydrocarbyl group such as arylene; or a hydrocarbyl group containing silicon or germanium such as lower alkyl- or arylsilylene, or lower alkyl- or arylgermylene, which may be substituted by a hydrocarbyl group, provided that the total number of carbon atom is 1 to 30. Of these groups, lower alkylene, cycloalkylene, arylene and lower alkylsilylene are preferred. More preferably, $R^3$ is a methylene or ethylene group which can be substituted by a lower alkyl or lower alkylsilyl group, or a silylene group which may be substituted by a lower alkyl group.

X and Y independently represent, more specifically, hydrogen, a halogen (for example, fluorine, chlorine, bromine and iodine, preferably chlorine), a monovalent hydrocarbyl group having 1 to 20 carbon atoms or a monovalent hydrocarbyl group having 1 to 20 carbon atoms, containing silicon or germanium (preferably any of the hydrocarbyl groups enumerated previously as examples of $R^5$, and, in particular, methyl). More preferably, X and Y independently represent a lower alkyl group or a lower alkyl-substituted silyl group.

A metallocene compound preferably used in the present invention is the one in which at least one of $R^1$, $R^2$, $R^3$, M, X and Y fulfills the following conditions:

$R^1$: a lower alkyl group;

$R^2$: a n-butylene group or a 1,3-butadienylene group;

$R^3$: a methylene or ethylene group which may be substituted with a lower alkyl or lower alkylsilyl group, or a silylene group which may be substituted with a lower alkyl group;

M: zirconium;

X and Y: independently chlorine, a lower alkyl group or a lower alkyl-substituted silyl group.

The typical synthesis route of the compound [I] of the present invention is as follows. In the following scheme, $HR^a$ represents:

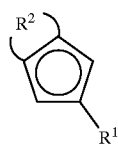

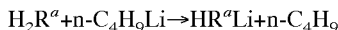
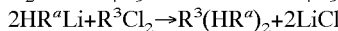
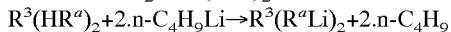
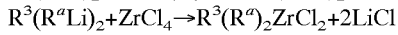

Nonlimitative examples of the above-described transition metallic compound are as follows. It is noted that although the compounds listed below are described simply by their chemical names, they are, as a matter of course, asymmetry in stereostructure as defined previously.

(1) ethylenebis-(2-methylindenyl)zirconium dichloride
(2) 1,1,2,2-tetraphenylethylenebis-(2-methylindenyl)zirconium dichloride
(3) dimethylsilylenebis-(2-methylindenyl)zirconium dichloride
(4) diphenylsilylenebis-(2-methylindenyl)zirconium dichloride
(5) dimethylgermylenebis-(2-methylindenyl)-zirconium dichloride
(6) ethylenebis-(2-methyltetrahydroindenyl)-zirconium dichloride
(7) 1,1,2,2-tetraphenylethylenebis-(2-methyltetrahydroindenyl)zirconium dichloride
(8) dimethylsilylenebis-(2-methyltetrahydroindenyl)zirconium dichloride
(9) diphenylsilylenebis-(2-methyltetrahydroindenyl)zirconium dichloride
(10) dimethylgermylenebis-(2-methyltetrahydroindenyl)zirconium dichloride
(11) ethylenebis-(2-ethylindenyl)zirconium dichloride
(12) 1,1,2,2-tetraphenylethylenebis-(2-ethylindenyl)zirconium dichloride
(13) dimethylsilylenebis-(2-ethylindenyl)zirconium dichloride
(14) diphenylsilylenebis-(2-ethylindenyl)zirconium dichloride
(15) ethylenebis-(2-ethyltetrahydroindenyl)zirconium dichloride
(16) ethylenebis-(2-n-propylindenyl)titanium dichloride
(17) ethylenebis-(2-methylindenyl)zirconiumdimethyl
(18) 1,1,2,2-tetraphenylethylenebis-(2-methylindenyl)zirconiumdimethyl
(19) dimethylsilylenebis-(2-methylindenyl)titaniumdimethyl
(20) ethylene(2-methylindenyl)(2-ethylindenyl)zirconium dichloride
(21) ethylene(2-methyltetrahydroindenyl)(2-ethyltetrahydroindenyl)zirconium dichloride
(22) ethylenebis-(2-trimethylsilylindenyl)zirconium dichloride
(23) dimethylsilylenebis-(2-cyclopropyltetrahydroindenyl)hafnium dichloride
(24) ethylenebis-(2-methyl-4-methylindenyl)hafnium dichloride
(25) ethylenebis-(2-methyl-5-methylindenyl)zirconium dichloride
(26) dimethylsilylenebis-(2-methylindenyl)zirconiummethyl(methylphenylamine)
(27) dimethylsilylenebis-(2-methylindenyl)zirconium butoxychloride
(28) dimethylsilylenebis-(2-methylindenyl)zirconium-bis(trimethylsilyl)
(29) dimethylsilylenebis-(2-methylindenyl)zirconium trimethylsilylchloride
(30) dimethylsilylenebis-(2-methylindenyl)zirconium-bis(trimethylsilyl)methylchloride
(31) ethylenebis-(2,6-dimethylindenyl)zirconium dichloride
(32) ethylenebis-(2,7-dimethylindenyl)zirconium dichloride
(33) dimethylsilylenebis-(2,4-dimethylindenyl)zirconium dichloride
(34) dimethylsilylenebis-(2,5-dimethylindenyl)zirconium dichloride
(35) dimethylsilylenebis-(2,6-dimethylindenyl)zirconium dichloride
(36) dimethylsilylenebis-(2,7-dimethylindenyl)zirconium dichloride
(37) dimethylsilylenebis-(2,4,7-trimethylindenyl)zirconium dichloride
(38) dimethylsilylenebis-(2,4,7-trimethyl-4,5,6,7-tetrahydroindenyl)zirconium dichloride <Component (B)>

The other component (component (B)) for use in the present invention is alumoxane represented by the following formula [II] or [III]:

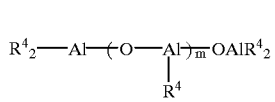

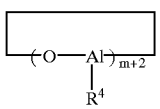

[III]

wherein m is a number of 4 to 30, preferably 10 to 25, and $R^4$ is a hydrocarbyl group, preferably a hydrocarbyl group having 1 to 10 carbon atoms, more preferably 1 to 4 carbon atoms.

The above component (B) is a product obtained from one type of trialkylaluminum or by a reaction between two or more types of trialkylaluminum and water. Specific examples of the component (B) include (a) methylalumoxane, ethylalumoxane, propylalumoxane, butylalumoxane and isobutylalumoxane which are obtainable from one type of trialkylaluminum; and (b) methylethylalumoxane, methylbutylalumoxane and methylisobutylalumoxane which can be obtained by a reaction between two types of trialkylaluminum and water. Of these compounds, methylalumoxane and methylisobutylalumoxane are particularly preferred.

It is also possible to use a plurality of the alumoxanes which are selected from one of the above groups or from both of the groups. Moreover, the above alumoxanes can be used in combination with other alkylaluminum compound such as trimethylaluminum, triethylaluminum, triisobutylaluminum or dimethylaluminum chloride.

The above alumoxanes can be prepared under the various known conditions. Specifically, the following methods can be mentioned:

(a) the method in which trialkylaluminum is directly reacted with water by using a proper organic solvent such as toluene, benzene or ether;

(b) the method in which trialkylaluminum is reacted with a salt hydrate containing water of crystallization, such as a hydrate of copper sulfate or of aluminum sulfate;

(c) the method in which trialkylaluminum is reacted with water impregnated in silica gel or the like;

(d) the method in which trimethylaluminum and triisobutylaluminum are mixed, and the mixture is directly reacted with water by using a proper organic solvent such as toluene, benzene or ether;

(e) the method in which trimethylaluminum and triisobutylaluminum are mixed, and the mixture is reacted, while heating, with a salt hydrate containing water of crystallization, such as a hydrate of copper sulfate or of aluminum sulfate;

(f) the method in which silica gel or the like that has been impregnated with water in advance is treated with triisobutylaluminum, and then subjected to an additional treatment with trimethylaluminum;

(g) the method in which methylalumoxane and isobutylalumoxane are synthesized separately by the known methods, mixed in the predetermined amounts, and reacted with each other while heating; and (h) the method in which a salt containing water of crystallization such as $CuSO_4 \cdot 5H_2O$ is added to an aromatic hydrocarbon solvent such as benzene or toluene, and reacted with trimethylaluminum at a temperature of approximately −40 to 40° C. In this method, the amount of water used is, in general, from 0.5 to 1.5 when expressed by the molar ratio to the trimethylaluminum. The methylalumoxane thus obtained is a linear or cyclic organoaluminum polymer.

<Preparation of Catalyst>

The catalyst according to the present invention can be prepared by bringing the above-described component (A) and component (B) into contact with each other in the presence or absence of monomers to be polymerized, inside or outside an autoclave.

No particular limitation is imposed on the amounts of the components (A) and (B) for use in the present invention. For instance, in the case of solvent polymerization, the preferable range of the amount of the component (A) used is from $10^{-7}$ to $10^2$ mmol/lit. when calculated on the basis of the transition metal atom. It is preferable that the molar ratio of Al/transition metal be 100 or more, more preferably 500 or more, up to 100,000, most preferably 1000 or more, up to 50,000.

As mentioned previously, the catalyst of the present invention can contain some other components in addition to the components (A) and (B). Examples of a third component (optional component) which can be added to the components (A) and (B) include compounds containing active hydrogen such as $H_2O$, methanol, ethanol and buthanol, electron-donor-type compounds such as ether, ester and amine, and compounds containing alkoxyl such as phenyl borate, dimethylmethoxyaluminum, phenyl phosphate, tetraethoxysilane and diphenyldimethoxysilane.

When the above catalyst system is used for the polymerization of an olefin, the components (A) and (B) may be introduced into a reaction vessel either separately or after being brought into contact with each other.

Use of Catalyst/Polymerization of Olefin

The catalyst of the present invention is applicable not only to slurry polymerization using a solvent but also to polymerizations using substantially no solvent such as liquid-phase-non-solvent polymerization, gas-phase polymerization and solution polymerization. Moreover, the catalyst of the invention can also be applied to continuous polymerization and batch polymerization.

In the case of slurry polymerization, saturated aliphatic and aromatic hydrocarbons such as hexane, heptane, pentane, cyclohexane, benzene and toluene are used as a solvent either singly or in combination of two or more.

The approximate range of the polymerization temperature is from −78 to 200° C., preferably from −20 to 100° C. There is no limitation on the olefin pressure of the reaction system. However, the preferable range of the pressure is from atmospheric pressure to 50 kg/cm²G.

The molecular weight of the finally obtainable polymer can be controlled by any known method, for instance, by properly selecting the temperature or pressure for the polymerization, or by the introduction of hydrogen.

Olefins which can be polymerized by the catalyst of the present invention, that is, olefins which are used for the polymerization reaction in the method of the present invention are α-olefins having 2 to 20, preferably 2 to 10 carbon atoms. Specific examples of such α-olefins include propylene, 1-butene, 4-methyl-1-pentene, 1-hexene, 1-octene, 1-decene, 1-dodecene, 1-tetradecene, 1-hexadecene, 1-octadecene and 1-eicosene. Of these α-olefins, propylene is particularly preferred. A mixture of two or more of the above α-olefins can also be used for the polymerization.

By using the catalyst of the present invention, the above α-olefins can also be copolymerized with ethylene. Moreover, the catalyst of the invention is also useful for the copolymerization of the above α-olefins and other monomers which can be copolymerized with the α-olefins, for example, conjugate and non-conjugate dienes such as butadiene, 1,4-hexadiene, 1,8-nonadiene and 1,9-decadiene, and cyclic olefins such as cyclopropene, cyclobutene, cyclohexene, norbornene and dicyclopentadiene.

The present invention will now be described more specifically with reference to Examples. However, the following Examples should not be construed as limiting the present invention.

EXAMPLE 1

Synthesis of ethylenebis-(2-methylindenyl) zirconium dichloride

All of the following reactions were carried out under an inert gas atmosphere. Solvents dried in advance were used for the reactions.

In a 500-ml glass reaction vessel, 4.3 g (33 mmol) of 2-methylindene was dissolved in 80 ml of tetrahydrofuran. 21 ml of a 1.6 M hexane solution of n-butyllithium was slowly added dropwise to the reaction vessel while cooling. The mixture was stirred at room temperature for one hour, and then cooled again. To this mixture, 3.1 g of 1,2-dibromoethane was slowly added dropwise, and the resulting mixture was stirred at room temperature for 12 hours. 50 ml of water was added to the mixture, and the organic phase was fractionated. After drying, the organic phase was washed several times with heptane, and dried to give 2.9 g of bis-(2-methylindenyl)ethane.

2.1 g (7.3 mmol) of the above-obtained bis-(2-methylindenyl)ethane was dissolved in 70 ml of tetrahydrofuran. To this solution, 9.2 ml of a 1.6 M hexane solution of n-butyllithium was slowly added dropwise while cooling. After stirring at room temperature for 3 hours, the mixture was slowly added dropwise to a solution consisting of 1.6 g (7.0 mmol) of zirconium tetrachloride and 60 ml of tetrahydrofuran. After stirring the mixture for 5 hours, hydrogen chloride gas was blown into the mixture, and the mixture was then dried. Subsequently, toluene was added to the mixture, and the soluble matter was fractionated and crystallized at a low temperature to give 0.95 g of a yellow powder.

By $^1$H-NMR, the compound thus obtained was identified to be ethylenebis-(2-methylindenyl)zirconium dichloride, and it was also confirmed that the two 2-methylindenyl groups contained in the compound were asymmetric, that is, the relationship between the two groups with respect to a plane containing zirconium atom was not equivalent to that between an object and its mirror image.

Synthesis of Alumoxane 50 g of $CuSO_4 \cdot 5H_2O$ was added, 5 g at a time at 5-minutes intervals, to 565 ml of toluene solution containing 48.2 g of trimethylaluminum placed in a reaction vessel at a temperature of 0° C. while stirring. After the addition was completed, the temperature of the mixture was gradually raised to 25° C., and a reaction was carried out at the temperature for 2 hours. The temperature of the reaction mixture was then raised to 35° C., and the reaction was continued at the temperature for 2 days. The remaining solid of the copper sulfate was filtered off, thereby obtaining a toluene solution of alumoxane. The density of the methylalumoxane obtained was found to be 27.3 mg/ml (2.7 w/v %).

Polymerization

A 1.5-liter agitation-type autoclave was thoroughly purged with propylene. 500 ml of toluene which had been thoroughly dehydrated and degassed to remove dissolved oxygen was introduced into the autoclave. To the toluene were added 10 mmol (calculated in terms of Al atom) of the above-obtained methylalumoxane and 1.0 μmol, of the above-prepared ethylenebis-(2-methylindenyl)zirconium dichloride. Thereafter, propylene was introduced into the mixture, and polymerized at a temperature of 20° C. for 15 minutes. Propylene was further introduced into the system, and the polymerization was continued for 2 hours at a temperature of 40° C. under an inner pressure of 7 kg/cm$^2$G. After the reaction was completed, the polymer slurry obtained was collected by filtration and dried to give 56.2 g of a polymer. The catalytic activity was 308 kg/polymer/g·Zr·hr.

The number-average molecular weight of the polymer was $9.60 \times 10^4$, the molecular weight distribution index "Q value (=Mw/Mn)" was 2.02, and the melting point of the polymer (the peak temperature of the DSC curve) was approximately 134.3° C.

Comparative Example 1

The procedure of Example 1 was repeated except that the ethylenebis-(2-methylindenyl)zirconium dichloride used in Example 1 was replaced by ethylenebis(indenyl)zirconium dichloride, whereby 80.9 g of a polymer was obtained. The catalytic activity was 445 kg-polymer/g·Zr·hr. The number-average molecular weight of the polymer was $2.13 \times 10^4$, the molecular weight distribution index (Q value) was 2.04, and the melting point of the polymer was approximately 135.2° C.

Neither extrusion molding nor injection molding was applicable to the polymer.

Comparative Example 2

The procedure of Example 1 was repeated except that the ethylenebis-(2-methylindenyl)zirconium dichloride used in Example 1 was replaced by ethylenebis(indenyl)hafnium dichloride, whereby 12.1 g of a polymer was obtained. The catalytic activity was 33.6 kg-polymer/g·Hf·hr. The number-average molecular weight of the polymer was $1.20 \times 10^5$, the molecular weight distribution index (Q value) was 2.63, and the melting point of the polymer was 134.8° C.

EXAMPLE 2

The procedure of Example 1 was repeated except that 5 ml of 1-hexene was added before introducing the ethylenebis-(2-methylindenyl)zirconium dichloride, whereby 51.2 g of a polymer was obtained. The catalytic activity was 281 kg-polymer/g·Zr·hr. The number-average molecular weight of the polymer was $7.89 \times 10^4$, the molecular weight distribution index (Q value) was 1.90, the hexene content of the polymer was 0.59 mol %, and the melting point of the polymer was 131.4° C.

EXAMPLE 3

Synthesis of dimethylsilylenebis-(2-methylindenyl) zirconium dichloride

In a 500-ml glass reaction vessel, 4.3 g (33 mmol) of 2-methylindene was dissolved in 80 ml of tetrahydrofuran. 21 ml of a 1.6 M hexane solution of n-butyllithium was slowly added dropwise to the reaction vessel while cooling. The mixture was stirred at room temperature for one hour, and then cooled again. To this mixture, 2.1 g of dimethyl-dichlorosilane was slowly added dropwise, and the resulting mixture was stirred at room temperature for 12 hours. 50 ml of water was added to the mixture, and the organic phase was fractionated and dried to give 3.5 g of dimethylbis-(2-methylindenyl) silane.

3.5 g of the above-obtained dimethylbis-(2-methylindenyl)silane was dissolved in 70 ml of tetrahydrofuran. To this solution, 13.9 ml of a 1.6 M hexane solution of n-butyllithium was slowly added dropwise while cooling. After stirring at room temperature for 3 hours, the mixture was slowly added dropwise to a solution consisting of 2.6 g (11 mmol) of zirconium tetrachloride and 60 ml of tetrahydrofuran. After stirring the mixture for 5 hours, hydrogen chloride gas was blown into the mixture, and the mixture was then dried. Subsequently, methylene chloride was added to the mixture, and the soluble matter was fractionated and crystallized at a low temperature to give 0.45 g of an orange powder.

By $^1$H-NMR, the compound thus obtained was identified to be dimethylsilylenebis-(2-methylindenyl)zirconium dichloride, and it was also confirmed that the two 2-methylindenyl groups contained in the compound were asymmetric.

Synthesis of Alumoxane

To a 1,000-ml flask equipped with a stirrer and a reflux condenser and thoroughly purged with nitrogen, 100 ml of toluene which had been thoroughly dehydrated and degassed to remove dissolved oxygen was introduced. Subsequently, a solution of 0.72 g (10 mmol) of trimethylaluminum and 1.96 g (10 mmol) of triisobutylaluminum in 50 ml of toluene was introduced into one of two dropping funnels, and toluene containing saturated water was introduced into the other dropping funnel. While keeping the reaction system at 30° C., the solution of the aluminum mixture and the toluene containing saturated water were fed, by dropping an equimolar amount of Al and $H_2O$, to the reaction system over a period of 3 hours. After the feeding was completed, the temperature of the mixture was raised to 50° C., and a reaction was carried out at the temperature for two hours. After the reaction was completed, the solvent was evaporated under reduced pressure, thereby obtaining 1.9 g of a white solid. the white solid thus obtained was dissolved in toluene, and subjected to $^{13}$C-NMR. As a result, the ratio (methyl group):(isobutyl group) was found to be 1.16:1. Further, a spectrum showing a peak with a half band width of 6196 Hz having a chemical shift of 179 ppm was obtained by $^{27}$Al-NMR.

Polymerization

The procedure of Example 1 was repeated except that the ethylenebis-(2-methylindenyl)zirconium dichloride used in Example 1 was replaced by the above-obtained dimethylsilylenebis-(2-methylindenyl)zirconium dichloride, and the methylalumoxane used in Example 1 was replaced by the above-synthesized methylisobutylalumoxane, thereby polymerizing propylene.

As a result, 95.4 g of a polymer was obtained. The catalytic activity was 524 kg-polymer/g·Zr·hr. The number-average molecular weight of the polymer was 19.0×10$^4$; the molecular weight distribution index (Q value) was 2.04; and the melting point of the polymer was 149.4° C.

EXAMPLE 4

The procedure of Example 3 was repeated except that the polymerization was carried out at a temperature of 70° C., whereby 113.4 g of a polymer was obtained. The catalytic activity was 621 kg-polymer/g·Zr·hr. The number-average molecular weight of the polymer was 7.50×10$^4$; the molecular weight distribution index (Q value) was 1.98; and the melting point of the polymer was 139.2° C.

Comparative Example 3

The procedure of Example 3 was repeated except that the dimethylsilylenebis-(2-methylindenyl)zirconium dichloride used in Example 3 was replaced by dimethylsilylenebis (indenyl)zirconium dichloride, whereby 113 g of a polymer was obtained. The catalytic activity was 618 kg-polymer/g·Zr·hr. The number-average molecular weight of the polymer was 4.06×10$^4$; the molecular weight distribution index (Q value) was 2.06; and the melting point of the polymer was 142.3° C.

Comparative Example 4

The procedure of Example 3 was repeated except that the dimethylsilylenebis-(2-methylindenyl)zirconium dichloride used in Example 3 was replaced by dimethylsilylene(2,4-dimethylcyclopentadienyl)(3',5'-dimethylcyclopentadienyl) zirconium dichloride which is the same compound as that used in Example 2 of Japanese Patent Laid-Open Publication No. 12406/1991, thereby polymerizing propylene. As a result, 108 g of a polymer was obtained. The catalytic activity was 593 kg-polymer/g·Zr·hr. The number-average molecular weight of the polymer was 4.29×10$^4$.

EXAMPLE 5

The procedure of Example 3 was repeated except that the methylisobutylalumoxane used in Example 3 was replaced by the methylalumoxane synthesized in Example 1, thereby polymerizing propylene. As a result, 45.1 g of a polymer was obtained. The catalytic activity was 248 kg-polymer/g·Zr·hr. The number-average molecular weight of the polymer was 14.3×10$^4$, and the molecular weight distribution index (Q value) was 2.11.

What is claimed is:
1. A transition metal compound having formula (I):

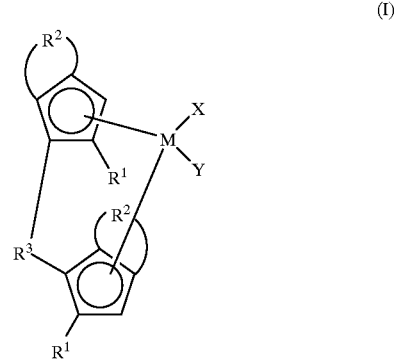

(I)

wherein: M represents a transition metal selected from the group consisting of titanium, zirconium, and hafnium;
two $R^1$s may be the same or different, and each represents a monovalent hydrocarbyl group having 1 to 4 carbon atoms or a monovalent hydrocarbyl group having 1 to 4 carbon atoms and containing silicon;
$R^2$ contains up to 20 carbon atoms and is selected from the group consisting of 1,3-butadienylene substituted with 1 to 2 alkyl groups and phenyl-1,3-butadienylene;

$R^3$ is selected from the group consisting of a methylene group, an ethylene group, and a silylene group which may be substituted by up to two groups selected from the group consisting of lower alkyl and phenyl; and X and Y independently represent a member selected from the group consisting of chlorine, lower alkyl, and a lower alkyl substituted silyl group, provided that the two five-membered cyclic ligands each having the substituents $R^1$ and $R^2$ are asymmetric about a plane containing M when viewed from their relative position in terms of the group $R^3$, and said transition metal compound being useful as a catalyst component for polymerizing olefins.

2. A transition metal compound of claim 1, wherein $R^2$ is methyl-1,3-butadienylene.

3. A transition metal compound of claim 1, wherein $R^2$ is phenyl-1,3-butadienylene.

4. A transition metal compound of claim 1, wherein M is titanium.

5. A transition metal compound of claim 1, wherein M is zirconium.

6. A transition metal compound of claim 1, wherein M is hafnium.

7. A transition metal compound according of claim 1, wherein the transition metal compound having the formula (I) is ethylenebis(2,5-dimethylindenyl)zirconium dichloride.

8. A transition metal compound according of claim 1, wherein the transition metal compound having the formula (I) is dimethylsilylenebis(2,4-dimethylindenyl)zirconium dichloride.

9. A transition metal compound according of claim 1, wherein the transition metal compound having the formula (I) is dimethylsilylenebis(2,5-dimethylindenyl)zirconium dichloride.

10. A transition metal compound according of claim 1, wherein the transition metal compound having the formula (I) is ethylenebis(2,4-dimethylindenyl)hafnium dichloride.

11. A transition metal compound according of claim 1, wherein the transition metal compound having the formula (I) is dimethylsilylenebis(2-methyl, 4-phenyl-indenyl) zirconium dichloride.

12. A transition metal compound according of claim 1, wherein the transition metal compound having the formula (I) is dimethylsilylenebis(2,4,7-trimethylindenyl)zirconium dichloride.

* * * * *